United States Patent [19]
Nghiem et al.

[11] Patent Number: 5,869,301
[45] Date of Patent: Feb. 9, 1999

[54] METHOD FOR THE PRODUCTION OF DICARBOXYLIC ACIDS

[75] Inventors: Nhuan Phu Nghiem, Knoxville, Tenn.; Mark Donnelly, Warrenville, Ill.; Cynthia S. Millard, Plainfield, Ill.; Lucy Stols, Woodridge, Ill.

[73] Assignee: Lockhead Martin Energy Research Corporation, Oak Ridge, Tenn.

[21] Appl. No.: 792,655

[22] Filed: Jan. 31, 1997

Related U.S. Application Data

[63] Continuation-in-part of Ser. No. 556,805, Nov. 2, 1995.

[51] Int. Cl.$^6$ .................................. C12P 7/40; C12P 7/54
[52] U.S. Cl. ......................... 435/136; 435/140; 435/142; 435/145; 435/146; 435/161; 435/252.33; 435/252.8; 435/252.9; 435/853; 435/849
[58] Field of Search ....................... 435/142, 145, 435/140, 146, 161, 252.8, 252.33, 252.9, 853, 849, 136

[56] References Cited

U.S. PATENT DOCUMENTS

| | | | |
|---|---|---|---|
| 3,912,586 | 10/1975 | Kaneyuki et al. | 435/142 |
| 4,190,495 | 2/1980 | Curtiss, III. | |
| 4,624,920 | 11/1986 | Inoue et al. | 435/142 |
| 4,871,667 | 10/1989 | Imada et al. | 435/142 |
| 5,143,833 | 9/1992 | Datta | 435/145 |
| 5,143,834 | 9/1992 | Glassner et al. | 435/145 |
| 5,168,055 | 12/1992 | Datta et al. | 435/145 |
| 5,182,199 | 1/1993 | Hartley. | |
| 5,403,721 | 4/1995 | Ward et al.. | |
| 5,416,020 | 5/1995 | Severson et al.. | |
| 5,457,040 | 10/1995 | Jarry et al. | 435/142 |
| 5,504,004 | 4/1996 | Guettler et al. | 435/145 |
| 5,521,075 | 5/1996 | Guettler et al. | 435/145 |

OTHER PUBLICATIONS

Fairoz Mat–Jan, Kiswar Y. Alam and David P. Clark, "Mutants of *Escherichia coli* Deficient in the Fermentative Lactate Dehydrogenase", *J. of Bacteriology,* Jan. 1989, pp. 342–348.

Lene Juel Rasmussen, Peter Lange Moller and Tove Atlung, Carbon Metabolism Regulates Expression of the pfl (Pyruvate Formate–Lyase) Gene in *Escherchia coli, J. of Bacteriology,* Oct. 1991, pp. 6390–6397.

*Primary Examiner*—Herbert J. Lilling
*Attorney, Agent, or Firm*—Shelly S. Stafford

[57] ABSTRACT

The present invention is an economical fermentation method for the production of carboxylic acids comprising the steps of a) inoculating a medium having a carbon source with a carboxylic acid-producing organism; b) incubating the carboxylic acid-producing organism in an aerobic atmosphere to promote rapid growth of the organism thereby increasing the biomass of the organism; c) controllably releasing oxygen to maintain the aerobic atmosphere; d) controllably feeding the organism having increased biomass with a solution containing the carbon source to maintain the concentration of the carbon source within the medium of about 0.5 g/L up to about 1 g/L; e) depriving the aerobic atmosphere of oxygen to produce an anaerobic atmosphere to cause the organism to undergo anaerobic metabolism; f) controllably feeding the organism having increased biomass a solution containing the carbon source to maintain the concentration of the carbon source within the medium of $\geq 1$ g/L; and g) converting the carbon source to carboxylic acids using the anaerobic metabolism of the organism.

20 Claims, 7 Drawing Sheets

METHOD FOR THE PRODUCTION OF DICARBOXYLIC ACIDS

CROSS-REFERENCED APPLICATIONS AND PATENTS

The present application is a Continuation-In-Part of U.S. patent application Ser. No. 08/556,805 filed Nov. 2, 1995, incorporated herein by reference.

This invention was made with Government support under contract DE-AC05-96OR22464 awarded by the U.S. Department of Energy to Lockheed Martin Energy Research Corporation, and under contract no. W-31-109-ENG-38 between the U.S. Department of Energy and the University of Chicago representing Argonne National Laboratory, the Government has certain rights in this invention.

FIELD OF THE INVENTION

The present invention relates to a method for the production of dicarboxylic acids, particularly a fermentation method using a strain of *Escherichia coli* to produce high quantities of dicarboxylic acids such as malic acid, fumaric acid and succinic acid.

BACKGROUND OF THE INVENTION

Carboxylic acids and derivatives thereof are widely used as specialty chemicals for applications in polymers, foods, pharmaceuticals, and cosmetics. Succinic acid, for example, is useful for the production of such plastic precursors as 1,4-butanediol (BDO), tetrahydrofuran, and gammabutyrolactone. New products derived from succinic acid are under continual development, including the development of polyester. Polyester is made by linking succinic acid and BDO. Generally, esters of succinic acids have the potential of being new, "green" solvents that can supplant more harmful solvents and serve as precursors for millions of pounds of chemicals annually at a total market value of over one billion dollars.

The production of carboxylic acids, such as malic acid, succinic acid and fumaric acid, from renewable feedstocks (in this case through fermentation processes) is an avenue to supplant the more energy intensive methods of deriving such acids from nonrenewable sources. Succinate is an intermediate for anaerobic fermentations by propionate-producing bacteria but those processes result in low yields and concentrations.

Many succinic acid-producing organisms have been isolated, such as the anaerobic rumen bacteria, *Bacteroides ruminicola* and *Bacteroides amylophilus*. However, rumen organisms are characteristically unstable in fermentation processes. Another succinic acid-producing organism is *Anaerobiospirillum succiniciproducens* (*A. succiniciproducens*). Several patents have been issued on the use of this organism to produce succinic acid in an anaerobic fermentation process. One such patent by Glassner et al, U.S. Pat. No. 5,143,834, outlines the use of this organism in fermentation processes to naturally produce succinic acid in moderate yields. However, fermentation processes using *A. succiniciproducens* have a number of problems. One problem is that the organism is a strict anaerobe, its cultivation must be performed in an environment absolutely free of oxygen. The propagation of this organism in a commercial fermentation plant is difficult and requires highly skilled workers. *A. succiniciproducens* is also difficult to handle even in laboratory-scale practice and tends to degenerate under unfavorable conditions. Its degeneracy cannot be reversed. The organism has never been used in a commercial fermentation process. In other words, production-scale fermentation experience with this particular organism is non-existent. Furthermore, the organism requires an external supply of carbon dioxide to achieve a high yield of succinic acid. In a fermentation process, a stream of pure carbon dioxide must be sparged into the fermentation broth. *A. succiniciproducens* produces a mixture of succinic and acetic acids at a succinate:acetate molar ratio of about 2. The presence of acetic acid at high concentrations in the fermentation broth increases the cost of succinic acid purification. Production of the acetate co-product illustrates that one-third of the expensive glucose is not converted to succinate. Furthermore, the *A. succiniciproducens* host strain has been shown to be not highly osmotolerant in that it does not tolerate high concentrations of salts and is further inhibited by moderate concentrations of product. Another problem that the use of *A. succiniciproducens* presents is that medium preparation for the inoculum requires the addition of tryptophan and also requires the mixing of four different solutions, one of which contains corrosive and toxic $H_2S$.

It has long been known that a mixture of acids are produced from *E. coli* fermentation, as elaborated by J. L. Stokes in 1949 "Fermentation of glucose by suspensions of *Escherichia coli*," *J. Bacteriol.* 57:147–158. However, for each mole of glucose fermented, only 1.2 moles of formic acid, 0.1–0.2 moles of lactic acid, and 0.3–0.4 moles of succinic acid are produced. As such, efforts to produce carboxylic acids fermentatively have resulted in relatively large amounts of growth substrates, such as glucose, not being converted to desired product.

Fairoz Mat-Jan et al describes in the *J. Bacteriol.*, v. 171 (1989), pp. 342–348, a study conducted on mutants of *Escherichia coli* deficient in the fermentative AND-linked lactate dehydrogenase (ldh) that had been isolated showed no growth defects under anaerobic conditions unless present together with a defect in pyruvate formate lyase (pfl). Double mutants (pfl ldh) were unable to grow anaerobically on glucose or other sugars even when supplemented with acetate, whereas pfl mutants can do so. The study did not discuss nor did it investigate the production of succinic acid or dicarboxylic acids.

Although the succinate ion is a common intermediate in the metabolic pathway of several anaerobic microorganisms, a need exists in the art for a fermentation process to economically produce succinic acid as well as other carboxylic acids such as malic acid and fumaric acid, in large amounts or with high yields. The process should utilize low cost nutrients and substrates, the rate of fermentation should be high for high productivity, and the product concentration in the fermentation broth should be high.

OBJECTS OF THE INVENTION

Accordingly, it is an object of the present invention to provide an improved, practical and economical method for the production of dicarboxylic acids that overcome the disadvantages and problems presented by the prior art.

It is another object of the present invention to provide an improved, practical and economical method for the production of succinic acid, malic acid and fumaric acid with high yields.

It is yet another object of the present invention to provide a fermentation method utilizing an *Escherichia coli* mutant for the production of succinic acid, malic acid and fumaric acid with high yields.

It is still yet another object of the present invention to provide an improved, practical and economical fermentation method utilizing an *Escherichia coli* mutant for the production of succinic acid, malic acid and fumaric acid with high yields wherein the fermentation method is carried out in a single vessel, permitting precise control of oxygenation, glucose levels, pH and the rates of addition of nutrients.

Further and other objects of the present invention will become apparent from the description contained herein.

SUMMARY

In accordance with one aspect of the present invention, the foregoing and other objects are achieved by a method for producing carboxylic acids comprising the steps of a) inoculating a medium having a carbon source with a carboxylic acid-producing organism; b) incubating the carboxylic acid-producing organism in an aerobic atmosphere to promote rapid growth of the organism thereby increasing the biomass of the organism; c) controllably releasing oxygen to maintain the aerobic atmosphere; d) controllably feeding the organism having increased biomass with a solution containing the carbon source to maintain the concentration of the carbon source within the medium of about 0.5 g/L up to about 1 g/L; e) depriving the aerobic atmosphere of oxygen to produce an anaerobic atmosphere to cause the organism to undergo anaerobic metabolism; f) controllably feeding the organism having increased biomass a solution containing the carbon source to maintain the concentration of the carbon source within the medium of $\geq 1$ g/L; and g) converting the carbon source to carboxylic acids using the anaerobic metabolism of the organism.

In accordance with another aspect of the present invention, other objects are achieved by a method for producing carboxylic acids comprising the steps of a) inoculating a medium having a carbon source with a carboxylic acid-producing organism; b) incubating the organism in an environment having a maintained pH value and having an aerobic atmosphere to promote rapid growth of the organism thereby increasing the biomass of the organism; c) controllably releasing oxygen to maintain the aerobic atmosphere; d) controllably feeding the organism a solution containing the carbon source to maintain a concentration of carbon source within the medium of about 0.5 g/L up to about 1 g/L; e) transferring the organism having increased biomass to a production fermenter having an anaerobic atmosphere to cause the organism to undergo anaerobic metabolism; f) controllably feeding the organism a solution containing the carbon source to maintain a concentration of the carbon source within the production fermenter of $\geq 1$ g/L; and g) converting the carbon source to carboxylic acids using the anaerobic metabolism of the organism.

BRIEF DESCRIPTION OF THE DRAWINGS

For a better understanding of the present invention, together with other and further objects, advantages and capabilities thereof, reference is made to the following disclosure and appended claims when read in connection with the appended drawings, wherein:

DETAILED DESCRIPTION OF THE INVENTION

Figure 1:
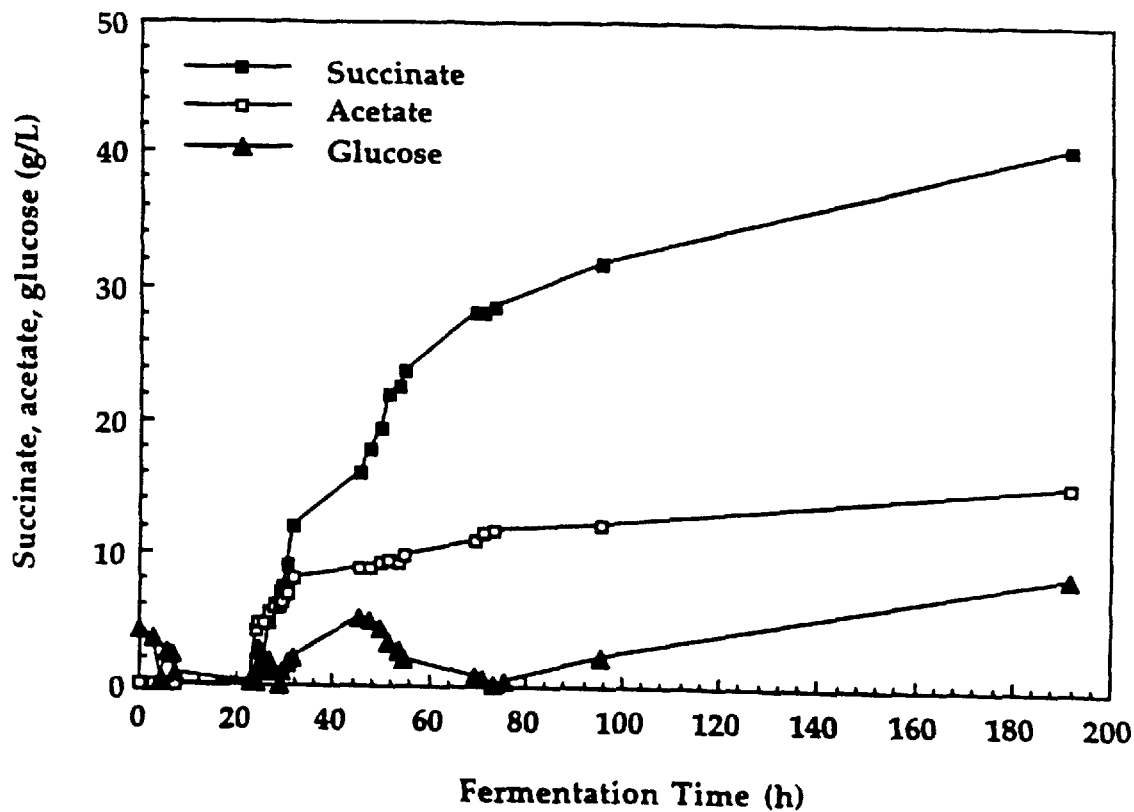
FIG. 1 shows the results of the experiment described in EXAMPLE 1.

The present invention is a novel, yet practical, economical means for producing high quantities of succinic acid, fumaric acid and malic acid in a controlled fermentation process. A strain of *Escherichia coli* (*E. coli*), referred to as AFP-111, has been utilized in the fermentation process of the present invention to overcome the problems presented by the art. AFP-111, a NZN-111 *E. coli* mutant, is a facultative organism. *E. coli* is very easy to handle. Its molecular biology and physiology have been known in great detail. Process improvement therefore can easily be achieved through molecular biology or modification of process parameters or both. Furthermore, *E. coli* has been used extensively in fermentation processes for the manufacture of biopharmaceuticals and chemicals. There exists a wealth of production-scale experience with this organism.

*E. coli* also produces a mixture of succinic and acetic acids, however, the molar ratio of succinate:acetate under non-optimized conditions is already about 3 or higher. This ratio can be increased substantially. Lower acetic acid concentrations in the fermentation broth will significantly reduce succinic acid purification cost. In addition, *E. coli* may not need an external supply of carbon dioxide to achieve a high yield of succinic acid. Without carbon dioxide sparging, the yield of succinic acid during the peak production period is comparable to that obtained with *A. succiniciproducens* with carbon dioxide sparging.

Normally under anaerobic conditions, wild type *E. coli* produces a mixture of fermentation products, of which succinic acid is a minor component. However, when AFP-111 is grown under anaerobic conditions, the major metabolic product is succinic acid. AFP-111 contains a unique spontaneous chromosomal mutation that produces a mixture of succinic acid, acetic acid and ethanol, with succinic acid as the major product. A maximum yield of 99 percent, weight of succinic acid per weight of glucose is produces with AFP-111. The use of AFP-111 could significantly reduce the cost of producing succinic acid by fermentation processes.

The *E. coli* fermentation process consists of two stages. In the first, the AFP-111 strain was grown under aerobic conditions, in a low glucose environment, to high cell density in the fermenter. In the present invention, glucose is used as a carbon source for both growth of the organism's biomass and for production of dicarboxylic acids. When the desired cell density was achieved, the air supply was cut off to force the organism to switch to its anaerobic metabolism, which resulted in the production of dicarboxylic acids, including malic, fumaric and succinic acid as the final end product. In one embodiment of the present invention, this two-stage fermentation process occurs in a single vessel.

The biochemical pathway of succinic acid production in *E. coli* involves a series of conversion steps. Pyruvic acid is converted first to oxaloacetic acid, then to malic acid, fumaric acid, and finally, to succinic acid. Of these acids, malic acid, fumaric acid and succinic acid are industrially important. AFP-111 accumulates succinic acid as the final product. If fumaric acid is the desired product, the gene which codes for the enzyme responsible for the conversion of fumaric acid to succinic acid is deleted and the resulting organism will accumulate fumaric acid instead of succinic acid. Similarly, if malic acid is the desired product, the gene which codes for the enzyme responsible for the conversion of malic acid to fumaric acid is deleted to make a malic acid-producing organism. With the current state-of-the-art molecular biology techniques and the knowledge of the entire *E. coli* linkage map, the deletion of a particular gene is just a simple task. A fermentation process for succinic acid production is readily applied to the production of malic and fumaric acids using the malic acid-producing and fumaric acid-producing organisms, respectively.

The entire process is fed-batch. In this process, a concentrated glucose solution which also contains light steep water, as a source of organic nitrogen and growth factors, and inorganic nutrients, is fed to the fermenter at a sufficient rate as to maintain residual glucose concentration at or below 1 g/L. Low glucose concentration is necessary to prevent excessive formation of acetic acid. Formation of acetic acid to high concentrations during the aerobic growth phase will eventually stop the growth of the organism and high cell density cannot be achieved. During the anaerobic production phase, high acetic acid concentrations will decrease the rate of succinic acid production and can eventually stop it completely. The use of AFP-111 can significantly reduce the cost of producing succinic acid by fermentation processes.

The maintenance of low glucose concentration in commercial fermenters is easily achieved through computer control of glucose feed rate based on off-gas analysis or on-line glucose analysis. This has become a very common industrial practice.

Anaerobic fermentation is the most ancient pathway for obtaining energy from fuels such as glucose. In anaerobic cells it is the sole energy-producing process. In most facultative cells, it is an obligatory first stage in glucose catabolism, which is followed by aerobic oxidation of the fermentation products via the tricarboxylic acid cycle.

The most widely utilized type of fermentation is glycolysis with pyruvate produced as a penultimate product. The disposition of pyruvate depends on which genes are present in the organism. In the presence of lactate dehydrogenase enzyme, glycolysis terminates when pyruvate is reduced via NADH and $H^+$ to lactate. In the presence of pyruvate decarboxylase and alcohol dehydrogenase, ethanol is formed. In the presence of pyruvate formate lyase (pfl), fermentation terminates with the production of acetate, ethanol, and formate, or hydrogen plus carbon dioxide.

If a mutation or a plurality of mutations in a bacterial genome eliminates the genes in that organism responsible for the catabolism of pyruvate, then pyruvate will accumulate. In anaerobically growing *E. coli*, those genes are pyruvate formate lyase (pfl) and lactate dehydrogenase (ldh). *E. coli* strain NZN 111, widely available to researchers from Dr. David Clark, Southern Illinois University, Carbondale, Ill. 62901, contains mutations in both genes whereby both pfl and ldh have been inactivated due to changes in the *E. coli* chromosomal DNA sequence. As such, NZN 111 cannot grow fermentatively. AFP-111, which was derived from NZN-111 by applying additional genetic changes, produces a mixture of succinic acid, acetic acid and ethanol under anaerobic conditions, with succinic acid being the major product.

It has been found that additional changes to NZN 111, occurring either spontaneously either during selective culturing or via plasmid transformation, ultimately result in the emergence of AFP-111 that produces succinic acid as a major product.

Spontaneous chromosomal mutations to NZN 111, which lead to AFP-111-type characteristics, occur when selective environments are utilized in serial culturing techniques. In a first step, NZN 111 biomass is increased aerobically on a rich medium, such as Luria Bertaini (LB) broth (0.5 percent yeast extract, 1 percent tryptone, and 1 percent NaCl, pH 7.5). Yields of between approximately $10^9$ to $10^{10}$ cells per milliliter are desirable. While incubation periods can vary, growth phase durations of between 5–7 hours, at 37° C., and at standard pressure produce the above-mentioned concentrations.

As a second step, the now accumulated biomass is subjected to anaerobic conditions rich in glucose to facilitate growth only of those cells (mutants) able to catabolize pyruvate. For example, cells are spread on 1.5 percent Agar plates containing approximately 1 to 30 grams per liter (g/l) of glucose, preferably 10 g/l glucose, and 30 micrograms ($\mu$g)/ml of Kanamycin. The gene for Kanamycin resistance is inserted into the gene for lactate dehydrogenase in NZN 111. Cultures are grown for 24 hours at 37° C., in a controlled anaerobic atmosphere. One anaerobic atmosphere producing good results was a mixture of carbon dioxide and hydrogen, which was provided through the use of an atmosphere control device commercially available from Becton-Dickinson, Cockeysville, Md. as GASPAK™.

The incubation period yielded many colonies of AFP 111 (approximately 2 per $10^7$ cells) and approximately half of those were capable of growing in liquid medium to produce the desired mixture of products.

In the instance of plasmid transformation, when NZN 111 is transformed with the plasmid pMDH13 containing the gene mdh for a mutant malate dehydrogenase enzyme, pyruvate catabolism resumes to produce lactate. Serial culturing of this transformant (NZN 111 (pMDH13)) results in AFP 111 containing a spontaneous chromosomal mutation. AFP 111 produces a mixture of succinic acid, acetic acid and ethanol as fermentation products, with succinic acid being produced up to 99 percent by weight compared to the weight of the glucose used in the growth medium. The development and transformation protocol of pMDH 13 is similar to that disclosed in W. E. Boernke, et al. (Sep. 10, 1995) *Archives of Biochemistry and Biophysics* 322, No. 1 pp. 43–52, incorporated herein by reference.

For experimental evaluation of the strains described herein, cells are cultured aerobically in glucose-free growth medium (Luria Broth) until cell densities of between 0.5 and 10 $OD_{600}$ are reached.

Once this appropriate biomass of AFP 111 is reached, the cells are then injected or otherwise transferred into a sealed fermentation reaction chamber to be contained therein. The broth is mixed with glucose or some other suitable carbohydrate, such as xylose, galactose or arabinose at concentrations varying between approximately 10 to 30 g/l. The now-contained mixture is subjected to an atmospheric change whereby anaerobic conditions are achieved. One means for achieving the atmospheric change is through a gassing station whereby ambient air is exchanged for carbon dioxide.

Prior to introducing the mixture into the fermentation reaction chamber, the chamber is supplied with an appropriate amount of buffering medium, such as $MgCO_3$, $CaCO_3$ or $CaMg(CO_3)_2$ so as to maintain near neutral pH. Between approximately 4 and 8 weight percent of buffering medium is typically utilized for suitable buffering capacity. Especially good results are obtained when the buffering medium is present as a solid so as to confer a time-release buffering capacity to the fermenting liquor.

The above procedure results in high yields of succinic acid. For example, a 6:1 ratio of succinic acid to acetic acid by weight was obtained, with a 99 percent yield. The succinic acid to acetic acid ratio increases even further when fermentation is conducted in the presence of hydrogen gas in $H_2$ concentrations of between approximately 25 percent to 100 percent. These results indicate that unlike the state of the art organisms, the mutant AFP 111 uses exogenous hydrogen as a reductant. For example, when luria broth, glucose, buffering agent, and a mixture of hydrogen gas and carbon dioxide ($CO_2$ being liberated from the buffering agent) are present, succinic acid to acetic acid ratios approaching 9 are obtained. This result reflects another advantage of pinpointing the catabolism of glucose to desired product, without unwanted, acetate-producing side reactions.

Table 1 below illustrates the product distribution of the dicarboxylic acids for the original parent W1485 (also available from Southern Ilinois University), NZN 111 and AFP 111.

TABLE 1

Product yield in molar yield viz. initial glucose (mole percent) for AFP 111 and ancestors

| Product | Original Parent W1485 | Immediate Parent NZN 111 | Mutant AFP 111 |
| --- | --- | --- | --- |
| Succinic acid | 17 | 2 | 109 |
| Lactic acid | 24 | 0 | 0 |
| Pyruvic acid | 1 | 17 | 0 |
| Formic acid | 26 | 0 | 0 |
| Acetic acid | 51 | 6 | 49 |
| Ethanol | 80 | 15 | 47 |
| Total Product | 193% | 41% | 206%* |

*Molar yield values in theory can be 200 percent because one molecule of glucose can give two of all the products.

When a 100 percent carbon dioxide atmosphere is utilized, succinic acid production is enhanced with concentrations of succinic acid reaching approximately 45 grams per liter, productivity reaching approximately 1.6 grams per liter per hour, percent yield of grams of succinic acid to grams of glucose reaching 99 percent and the weight ratio of succinic acid to acetic acid reaching approximately six.

Succinic acid is also produced when the E. coli AND-dependent malic enzyme is produced in NZN 111 (by the addition and induction of the gene maeA). In this instance, the inducible plasmid pMEE2-1 is used to allow expression of the malic enzyme gene in the transformant NZN 111 (pMEE2-1).

Genomic DNA isolated from E. coli MC1061 was used as a template for cloning malic enzyme by PCR. The E. coli MC1061 was digested with restriction endonucleases Hind III and Pst I, with the resulting digested material sized on 1 percent TAE agarose gel. The size of the genomic DNA fragment containing the malic enzyme gene was determined using Southern Blot analysis with the PhotoGene Nucleic Acid Detection System (Cat. 8192SA), as described above.

Primers were based on published partial DNA sequence of the gene:

Sense: CGAAGAACAAGCGGAACGAGCAT;
Antisense: GGCAGCAGGTTCGGCATCITGTC;

These primers were combined at 1 microliter ($\mu$M) with approximately 20 nanograms (ng) of genomic DNA in a standard 100 microliter ($\mu$l) PCR reaction which produced the expected 0.8 kilobase (kb) internal fragment of the malic enzyme gene. The PCR product was purified using a Qiaex Gel Extraction Kit (Qiagen, Inc., Chatsworth, Calif.) and biotinylated using a BioNick Labeling System (GibcoBRL, Gaithersburg, Md). The biotinylated PCR product was used as the probe in the Southern Blot analysis of genomic E. coli DNA which had been cleaved with Hind III and one of several other second endonucleases. The malic enzyme gene was determined to be located in the region containing 2.0–2.5 kb fragments of Hind III and Pst I digested DNA One microgram of E. coli DNA was digested with Hind III and Pst I and sized on a preparative 1 percent TAE agarose gel. The E. coli DNA fragments in the 2.0–2.5 kb region were isolated and purified using the Qiaex Gel Extraction Kit. The purified DNA fragments were ligated into the polylinker region of pUC19 which had been cleaved with Pst I and Hind III and treated with shrimp alkaline phosphatase. The ligated material was then used as a template for a PCR reaction to amplify the entire malic enzyme gene. One microliter of the ligation mixture was used as a template with 1 $\mu$M of sense primer GATGCCCCATGGATATTCAAAAAAGAGTGAGT, which targeted the malic enzyme gene, and 0.25 $\mu$M of antisense primer TTTTCCCAGTCACGACGTTG, which targeted the ligated pUC19 DNA The amplification parameters were 94° C. denaturation, 55° C. hybridization for one minute and a 72° C. extension for three minutes for a total of 35 cycles. The PCR product was analyzed on a one percent TAE-agarose gel and the 1.8 kb fragment was isolated and purified using the Qiaex Gel Extraction Kit. A portion of the PCR product was digested with Bcl and Bgl to demonstrate that the product did contain the malic enzyme gene. The remainder of the PCR product was digested with Pst I and Nco I, gel isolated, repurified and then ligated into the polylinker region of the expression vector pTRC99a (Pharmacia, Piscataway, N.J.) which had been cleaved with Nco I and Pst I. E. coli strain NZN 111 was transformed with the ligation mixture by standard methods and the resulting colonies (four colonies from experimental and 2 colonies from control) were screened for the malic enzyme gene by restriction fragment analysis using Xmn (0.7 kb, 1.4 kb and 3.9 kb fragments expected). The plasmid containing the cloned malic enzyme gene was named pMEE3.

A 100 ml culture of NZN (pMEE3) was grown in an overnight culture and the plasmid was isolated using a Qiagen Plasmid Kit. The isolated plasmid was used as a template for PCR reaction. A new primer was designed to give an alternative N-terminus which was 81 base pairs down stream from the primer used in the first cloning of the malic enzyme. Twenty nanograms of plasmid was used as template with 1 $\mu$M of sense primer AGGATCCATGGAAC-CAAAAACAAAAAAC and antisense primer CGC-CAGGGTTTTCCCAGTCACGAC. The amplification parameters were the same as noted above. A portion of the PCR product was again verified by restriction mapping with Bcl I and Bgl II which verified that the product contained the malic enzyme gene. The remainder of the PCR material was digested with Pst I and Nco I and gel isolated, repurified and then ligated into the polylinker region of the expression vector pTRC99a (Pharmacia, Inc. Piscataway, N.J.) which had been cleaved with Nco I and Pst I. E. coli strain JM109 was transformed with the ligation mixture by standard methods and the resulting colonies (three experimental clones and 1 control clone) were screened for the desired insert by restriction ragment analysis. The plasmid containing this version of the malic enzyme gene was named pMEE2.

Thirty milliliters of LB broth containing 100 $\mu$g/ml ampicillin were inoculated with 1.5 mls of an overnight culture of pMEE2. After two hours of growth, the 30 ml culture was separated into 3×10 ml aliquots. Enzyme activity was induced with 0, 100 μM, and 10 μM isopropylthiogalactoside (IPTG). A 2 ml sample was removed from each culture at 0, 1, 2, 3, and 4 hours. Protein was isolated according to standard methods and the activity was determined as noted above.

Enzyme production, over time is depicted in Table 2 below:

TABLE 2

Malic enzyme production induced by IPTG in LB broth.

| Time (hour) | Without IPTG | 100 μM IPTG | 10 μM IPTG |
|---|---|---|---|
| | | μg/min/mg protein | |
| 0 | 3.09 | — | — |
| 1 | 4.83 | 26.5 | 5.84 |
| 2 | 4.26 | 38.2 | 10.06 |
| 3 | 8.46 | 75.3 | 32.7 |
| 4 | 9.92 | 88.2 | 38.95 |

Duplicate cultures of NZN 111 (pMEE2) and, as a control, NZN 111 (pTRC99a) were grown aerobically in 2 ml LB medium containing ampicillin. One culture of each was induced with 10 μM IPTG. After three hours, $OD_{600}$ had increased from 0.6 to 4.8. One milliliter of the cultures were injected into sealed 58 ml vials containing 10 ml of LB medium containing glucose at 20 g/L, acetate at 1 g/L and 0.5 g of solid $MgCO_3$. The atmosphere consisted of air:hydrogen:carbon dioxide in a 1:1:2 ratio at 1 atm pressure above ambient pressure. The culture was sampled immediately and at intervals during incubation at 37° C. with shaking at 100 rpm. Table 3 below provides a comparison of product yields when NZN 111 is transformed with raw vector (pTRC99a) versus pMEE2.

TABLE 3

Effect of expression of malic enzyme in NZN 111 (pMEE2) versus NZN 111 (pTRC99a)

| Product | Vector | maeA |
|---|---|---|
| | g/L | |
| Succinic Acid | 0.3 | 6.5 |
| Lactic Acid | 0.4 | 0.4 |
| Acetic Acid | 0 | 0 |
| Ethanol | 0 | 0.2 |

The results depicted in Table 3 are the result of incubation periods of between approximately 19 and 42 hours.

Malic acid, a precursor of succinic acid is in principle a better end product than succinic acid, in as much as its production requires one less reductive step. The theoretical stoichiometry for malic acid production is one mole of glucose and two moles of carbon dioxide converted to two moles of malic acid. As such, the production of malic acid could occur without waste of glucose. Fumaric acid, which is the dehydration product of malic acid and the precursor of succinate in the reduction pathway, could also be formed. Both malic acid and fumaric acid also could be formed without the production of co-product, but the higher solubility of malic acid makes it preferable for large scale production processes.

The transformation of suitable bacteria with a gene responsible for production of malic enzyme (such as maea) could result in a surplus of malate. Generally, the ideal bacteria would lack lactate dehydrogenase activity, and other enzymes which metabolize pyruvate, thereby resulting in an accumulation of pyruvate. The bacteria are instead transformed with maeA to directly produce malate. To maintain the high levels of malate produced, the bacteria must not be capable of converting the malate back to lactate, or on to fumarate or succinate. In as much as some Lactobacillus strains lack the malolactate enzyme, fumarase, and fumarate reductase responsible for such conversions, these strains are particularly suitable candidates for malate production in fermentation processes. The suitability of Lactobacillus is further enhanced given its very high osmotolerant characteristics. *Lactobacillus gasseri* is a near term host for such manipulation since it has been shown not to metabolize malate during the fermentation of glucose and is fairly well characterized genetically. *Lactobacillus casei* also holds considerable potential in as much as it exhibits relatively higher osmotolerance than *L. gasseri*.

Generally, a malic enzyme gene (such as maeA) in a suitable lactobacillus expression vector, such as pTRK327 induced in a lactobacillus host lacking a functional lactate dehydrogenase gene, would allow formation of malic acid. This could be achieved by insertion of the malic enzyme into the host's lactate dehydrogenase gene.

The chemicals used for the following examples for the production of carboxylic acids include: yeast extract and tryptone (Difco), glucose (A. E. Staley), light steep water (A. E. Staley corn processing plant in Loudon, Tn.), inorganic chemicals (E. Merck Science or J. T. Baker, reagent grade). The equipment used include: fermenter-1 L (Virtis), fermenter-5 L (New Brunswick, Bioflow 3000), pumps (Cole-Parmer, Master Flex), pH probes (Cole-Parmer), pH controllers (Cole-Parmer, Chem Cadet), dissolved oxygen meter (Cole-Parmer, 01971-00), dissolved oxygen probes (Ingold), autoclave (Amsco, Eagle 3000), shaker (New Brunswick), cryogenic vials (Cole Parmer).

The glucose analyzer came from Yellow Springs Instrument Company (YSI 2700 Select). In addition, the spectrophotometer for OD measurement is from Milton Roy (SPEC 21D).

*E. coi* strain AFP-111 was obtained from Argonne National Laboratory. The AFP-111 strain was derived from NZN-111. Stock culture was prepared by putting 1 g magnesium carbonate ($MgCO_3$) in a 250-mL flask, covering with a foam plug and autoclaving at 121° C. for 20 minutes. Next, a 500 mL medium was prepared containing tryptone 10 g/L, yeast extract 5 g/L, glucose 5 g/L, sodium chloride (NaCi) 10 g/L, potassium phosphate ($K_2HPO_4$) 7 g/L, potassium phosphate ($KH_2PO_4$) 3 g/L. The medium was then autoclaved at 121° C. for 20 minutes and allowed to cool to room temperature. Fifty milliliters of the medium was aseptically transferred to the first flask containing the magnesium carbonate. The flask was then inoculated with one full inoculation loop of AFP-111 from an agar slant sent from Argonne National Laboratory. The inoculated flask was then incubated in a shaker at 250 rpm at 37° C.

Then, a one liter medium was prepared containing tryptone 10 g/L, yeast extract 5 g/L, glucose 5 g/L, NaCl 10 g/L, $K_2HPO_4$ 7 g/L, $KH_2PO_4$ 3 g/L and magnesium sulfate ($MgSO_4$) 0.2 g/L. The medium was autoclaved at 121° C. for 20 minutes and allowed to cool. Then, 850 mL was aseptically transferred to a 1-liter fermenter.

When the 250 nL flask had been incubated for 16 hours, its entire contents were aseptically transferred to the 1-liter fermenter. The fermenter was maintained at 37° C. and at a pH of 7.0. Air was sparged into the bottom of the fermenter and the impeller speed was set at 500 rpm or higher to ensure sufficient oxygen transfer to the fermentation broth to avoid oxygen limitation. The pH was maintained at 7 by a pH controller which activated a pump on demand to add a base solution to the fermenter.

The base solution was prepared by putting 250 mL de-ionized water into a 500 mL graduated cylinder with a stir bar. The graduated cylinder was covered with two layers of autoclaving papercover and autoclaved at 121° C. for 20 minutes, then allowed to cool to room temperature. Next, 250 mL of 30% ammonium hydroxide ($NH_4OH$) was added. Then an oil overlay was added to prevent the escape of ammonia. The oil was autoclaved at 121° C. for 20 minutes before it was added to the cylinder. The solution was mixed by stirring on a magnetic plate. The resulted base solution was a 15% $NH_4OH$ solution.

To make a glycerol solution, 15 g of glycerol was placed in a small flask to which 15 mL deionized water was added. A small stir bar was added to the flask and then the flask was covered with a foam plug and mixed on a magnetic plate to make a 50% glycerol solution. The glycerol solution was autoclaved at 121° C. for 20 minutes, then allowed to cool to room temperature.

When the glucose concentration in the fermenter was about 1 g/L, 30 mL was aseptically removed from the fermenter and added to the 50% glycerol flask. Then the mixture was stirred on a magnetic plate. The mixture was then aseptically transferred to cryogenic vials (sterilized prior to packaging by manufacturer), about 1.2 mL per vial. The vials were sealed and stored in a −70° C. freezer. These vials served as AFP-111 stock culture for all the following examples.

EXAMPLE 1

The inoculum was raised in a shakeflask. The medium contained tryptone at 10 g/L, yeast extract at 5 g/L, glucose at 5 g/L, NaCl at 10 g/L, $K_2HPO_4$ at 14 g/L, $KH_2PO_4$ at 6 g/L, $(NH_4)_2SO_4$ at 2 g/L and $MgSO_4$ at 0.2 g/L. Fifty milliliters of the medium was placed in a 250 mL flask. The flask was stoppered, autoclaved at 121° C. for 20 minutes, cooled to room temperature and inoculated with 1 mL from a stock culture vial. It was then incubated at 37° C. at 200 rpm for 16 hours. The fermentation medium contained tryptone at 10 g/L, yeast extract at 5 g/L, glucose at 5 g/L, NaCl at 10 g/L, $K_2HPO_4$ at 1.4 g/L, $KH_2PO_4$ at 0.6 g/L, $(NH_4)_2SO_4$ at 2 g/L and $MgSO_4$ at 0.2 g/L. One liter of the medium was prepared, autoclaved at 121° C. for 20 minutes, and allowed to cool to room temperature before 850 mL was transferred to the one-liter fermenter. The fermenter was inoculated with the entire contents of the flask. (The fermentation medium contains low concentrations of glucose of less than 10 g/L). The fermentation was carried out at 37° C. and at a pH of 7.0 with aeration. The pH was maintained at 7.0 by adding a 15% $NH_4OH$ solution on demand through the action of a pH controller. When the initial glucose in the fermentation broth was exhausted, a feed pump was turned on to add a feed solution to the fermenter.

The feed solution (solution 1) was made by dissolving 250 g glucose and 50 g light steep water in 400 mL deionized water. This solution 1 was autoclaved at 121° C. for 20 minutes and cooled to room temperature. Then for solution 2, NaCl at 5 g/L, $K_2HPO_4$ at 7 g/L, $KH_2PO_4$ at 3 g/L, $(NH_4)_2SO_4$ at 22.5 g/L and $MgSO_4$ at 1 g/L were dissolved in 100 miL deionized water. The solution was then autoclaved at 121° C. for 20 minutes, cooled to room temperature and added to solution 1. The resulted solution was used as the feed to the fermenter.

The speed of the feed pump was manually controlled to keep the residual glucose concentration in the fermenter at or below 1 g/L. When the glucose concentration rose above 1 g/L, the pump speed was reduced. When the glucose concentration was too high, about 5 g/L or higher, the pump was turned off until the glucose concentration dropped below 1 g/L. During the first 24 hours, the fermenter was aerated to provide an aerobic environment which allowed the organism to grow to a high cell density. The optical density measured at 660 nm ($OD_{660}$) was 24 at 24 hours. The air then was turned off to establish an anaerobic environment to force the organism into anaerobic metabolism for succinic acid production. The anaerobic condition was maintained until the end of the experiment. During the anaerobic stage, the glucose concentration was maintained at or above 1 g/L.

The results of Example 1 are plotted in FIG. 1 and summarized below in TABLE 4.

TABLE 4

| | |
|---|---|
| Final succinic acid concentration (g/L) | 40.5 |
| Overall yield (g succinic acid/g glucose) | 0.54 |
| Yield during production phase (g succ. acid/g glucose) | 0.95 |
| Overall productivity (g/L-h) | 0.21 |
| Productivity during production phase (g/L-h) | 0.24 |
| Succinic acid concentration at 47 hours (g/L) | 17.9 |
| Productivity at 47 hours (g/L-h) | 0.38 |
| Final succinate:acetate molar ratio | 1.35 |

EXAMPLE 2

The experiment in this example was performed in exactly the same manner as in EXAMPLE 1, except that the air was turned off after six hours instead of after 24 hours. At the time the air was turned off, the $OD_{660}$ was 6.

Figure 2:
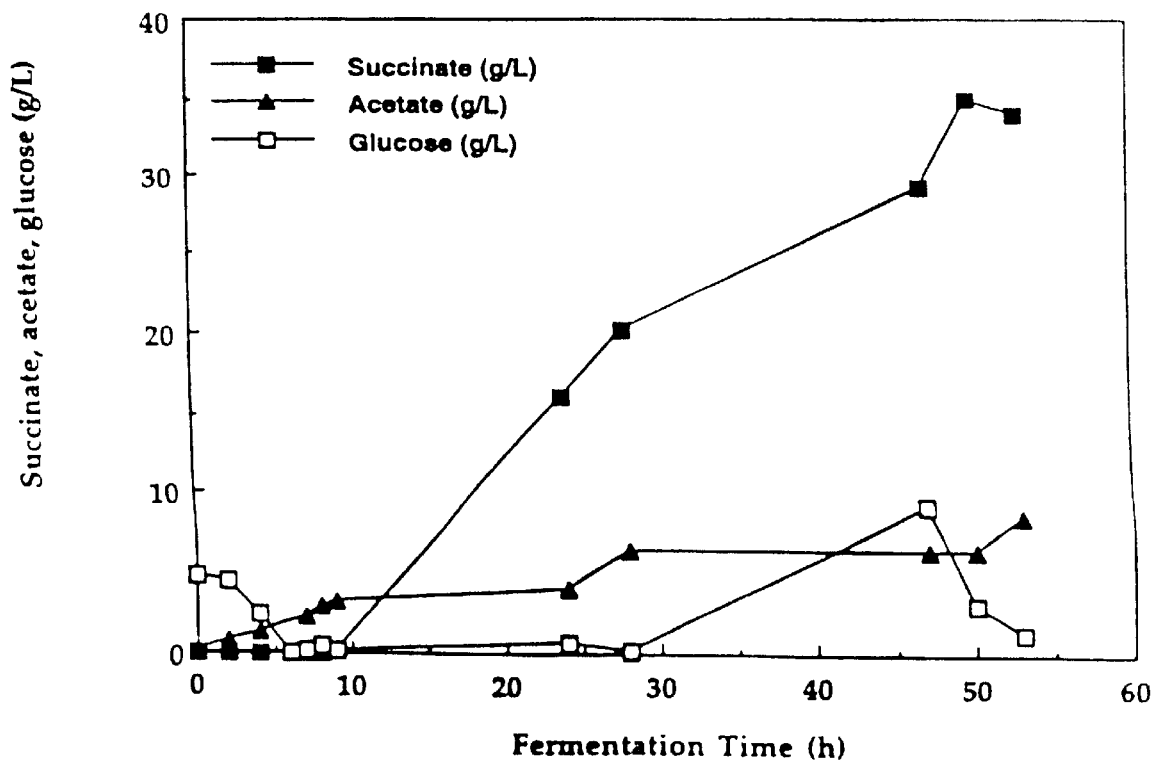
FIG. 2 shows the results of the experiment described in EXAMPLE 2.

The results are plotted in FIG. 2 and summarized in TABLE 5.

TABLE 5

| | | |
|---|---|---|
| Fermentation time (h) | 24 | 47 |
| Succinic acid concentration (g/L) | 16.0 | 29.20 |
| Productivity (g/L-h) | 0.67 | 0.62 |

The results indicated a significant improvement by earlier transition from aerobic to anaerobic conditions in the fermenter.

EXAMPLE 3

The medium used in this example contained the following: yeast extract at 2 g/L, tryptone at 15 g/L, NaCl at 2 g/L, $(NH_4)_2SO_4$ at 2 g/L, $CaCl_2$ at 0.6 g/L, $MgSO_4$ at 0.5 g/L, $KH_2PO_4$ at 1.3 g/L, $MnCl_2$ at 0.01 g/L. Four fermentations were performed in the five-liter fermenter. The pH in these experiments were controlled at 6.2, 6.6, 7.0 and 7.4 by adding 5N NaOH on demand. The inoculum was raised in a shakeflask using the same medium adjusted to pH 7.0. In the fermenters, the cells were grown aerobically with air sparging and impeller speed at 500 rpm until the $OD_{660}$ reached 6 (about 5 to 6 hours). Then agitation was reduced to 250 rpm and the sparge gas was changed to pure carbon dioxide.

Figure 3:
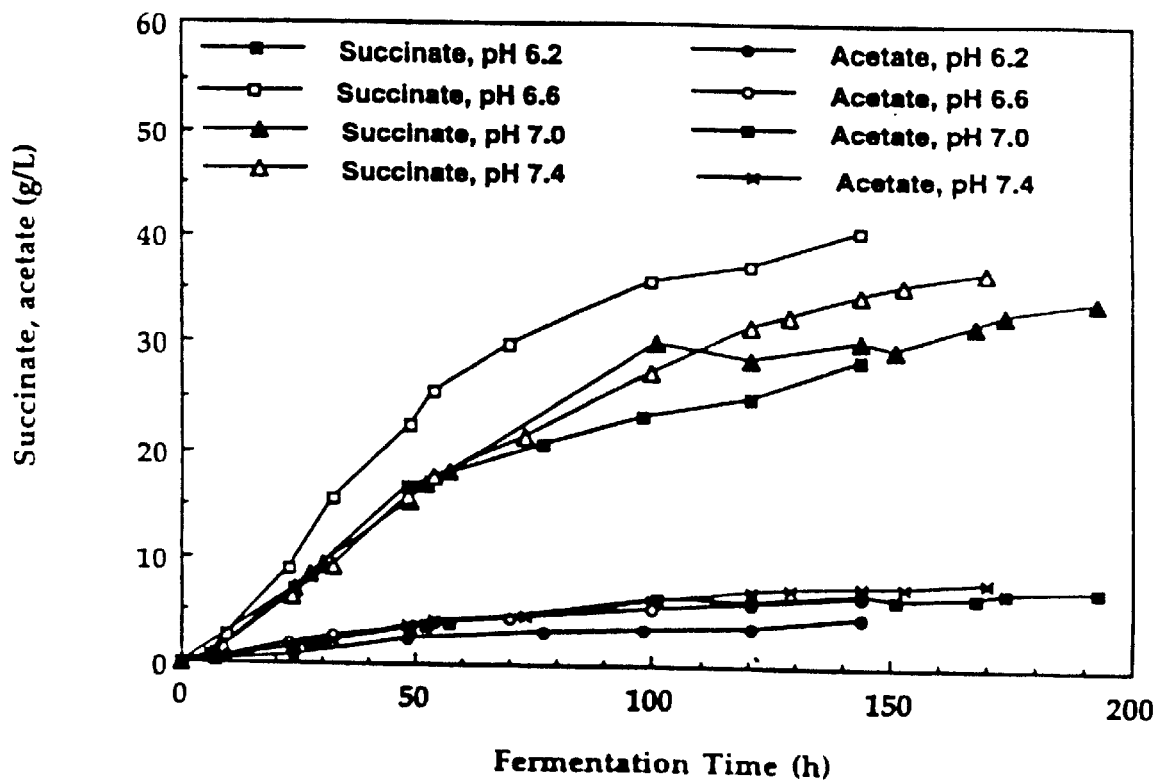
FIG. 3 shows the results of the experiment described in EXAMPLE 3.

The results to EXAMPLE 3 are plotted in FIG. 3 and summarized in TABLE 6. TABLE 6 is a comparison of fermentation results at 100 hours at different pH values.

TABLE 6

| pH | 6.2 | 6.6 | 7.0 | 7.4 |
|---|---|---|---|---|
| Succinic acid (g/L) | 23.3 | 35.7 | 30.1 | 27.5 |
| Acetic acid (g/L) | 3.3 | 5.3 | 6.3 | 6.0 |
| Glucose used (g) | 126 | 224 | 193 | 184 |
| Fermentation broth volume (L) | 3.6 | 4.3 | 4.4 | 4.5 |
| Yield (g succinic acid/g glucose) | 0.67 | 0.68 | 0.69 | 0.67 |
| Succinate:acetate molar ratio | 3.6 | 3.4 | 2.4 | 2.3 |

The results indicated that succinic acid could be produced over a wide range of pH, preferably at pH about 6.6 to 7.0.

EXAMPLE 4

In this example, both yeast extract and tryptone were replaced by light steep water, which is a very low-cost by-product of the corn processing industry. The light steep water was prepared by adjusting the pH of the steep water to 7.0 with 50% NaOH. The suspended solids were removed by filtration through Whatman filter paper No. 2. The clear filtrate was used in the fermentation experiment.

The inoculum was raised in a shakeflask. A solution was prepared with the following: NaCl at 20 g/L, $K_2PO_4$ at 28 g/L, $KH_2PO_4$ at 12 g/L, $(NH_4)_2SO_4$ at 4 g/L, $MgSO_4$ at 0.4 g/L. The solution was then autoclaved at 121° C. for 20 minutes. Then, 30 mL of the light steep water filtrate was added to a 250 mL flask. The flask was stoppered, autoclaved at 121° C. for 20 minutes and then allowed to cool to room temperature. Then to the flask, 30 mL of solution 1 (from EXAMPLE 1) was added. Therefore, this medium contained 50% light steep water filtrate. The flask was inoculated with 0.1 mL from a glycerol stock culture vial (EXAMPLE 1) and incubated at 35° C. and 200 rpm for 16 hours.

A solution 2 was prepared with the following: NaCl at 20 g/L, $K_2HPO_4$ at 2.8 g/L, $KH_2PO_4$ at 1.2 g/L, $(NH_4)_2SO_4$ at 4 g/L and $MgSO_4$ at 0.4 g/L. This solution then was autoclaved at 121° C. for 20 minutes and allowed to cool to room temperature. To the one-liter fermenter, 425 mL light steep water filtrate was added. The fermenter was autoclaved at 121° C. for 20 minutes and allowed to cool to room temperature. Then, 425 mL of solution 2 was added to the one-liter fermenter resulting in the fermentation medium to contain 50 light steep water filtrate. The fermenter was inoculated with the entire contents of the shakeflask. The fermentation was performed at 37° C. and at a pH 7.0. The pH was maintained at 7.0 by adding a 1.5M sodium carbonate solution on demand. This solution was sterilized by autoclaving at 121° C. The cells initially were grown aerobically by sparging air into the fermenter for six hours. Dissolved oxygen was monitored during this period. Occasionally the dissolved oxygen level dropped to below 5% of saturation, but with the continuous sparging of air, the condition inside the fermenter was still aerobic. At the end of that period, the air was turned off to start succinic acid production by anaerobic metabolism of the organism. At the same time, a pump was turned on to feed a solution containing about 500 g/L glucose to the fermenter. The speed of the feed pump was manually adjusted to keep the glucose concentration in the fermentation broth greater than or equal to 1 g/L.

Figure 4:
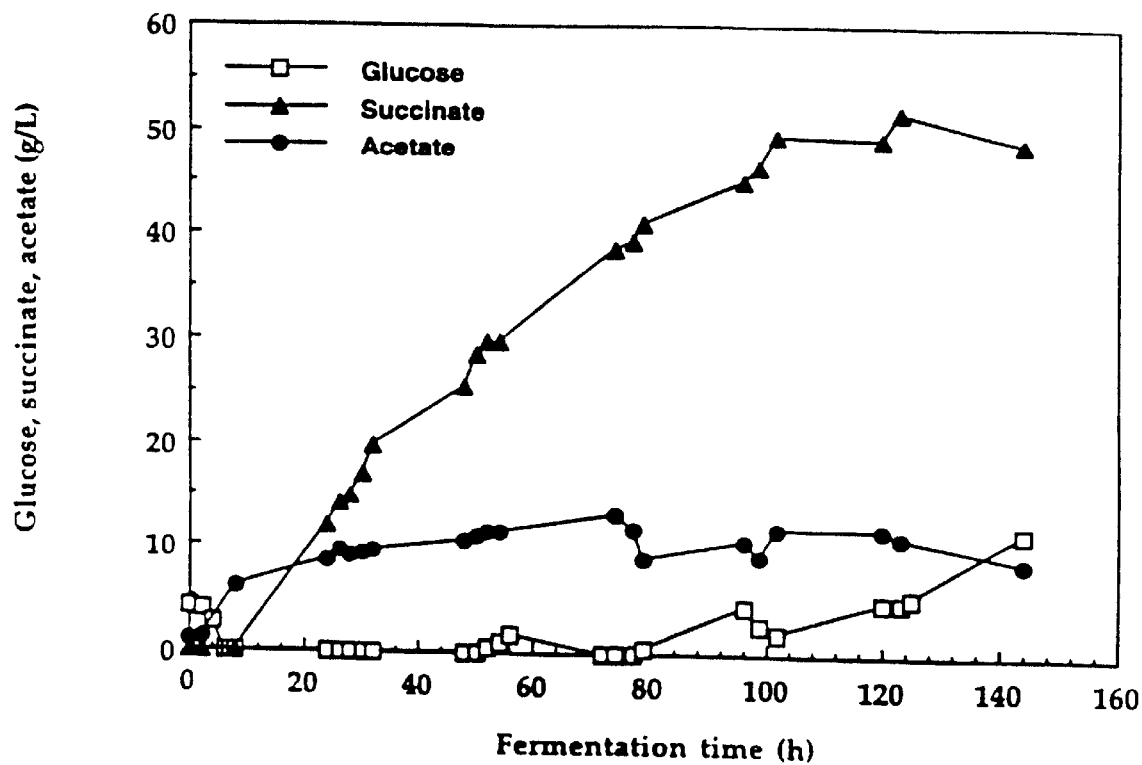
FIG. 4 shows the results of the experiment described in EXAMPLE 4.

The results of EXAMPLE 4 are plotted in FIG. 4 and summarized in TABLE 7. TABLE 7 shows the accumulation of succinic acid in 50% light steep water fermentation medium.

TABLE 7

| Fermentation time (h) | 24 | 48 | 99 |
|---|---|---|---|
| Succinic acid concentration (g/L) | 11.9 | 25.5 | 51.0 |
| Productivity (g/L-h) | 0.50 | 0.53 | 0.52 |

These results indicated that succinic acid could be produced in an inexpensive medium in which both the expensive yeast extract and tryptone were replaced by the low-cost light steep water.

EXAMPLE 5

In this example, the light steep water concentration in both the shakeflask and fermentation media was reduced to 25%. Other conditions were exactly the same as those described in EXAMPLE 4. Water was added to make up for the volume deficit due to the lesser quantities of light steep water used.

Figure 5:
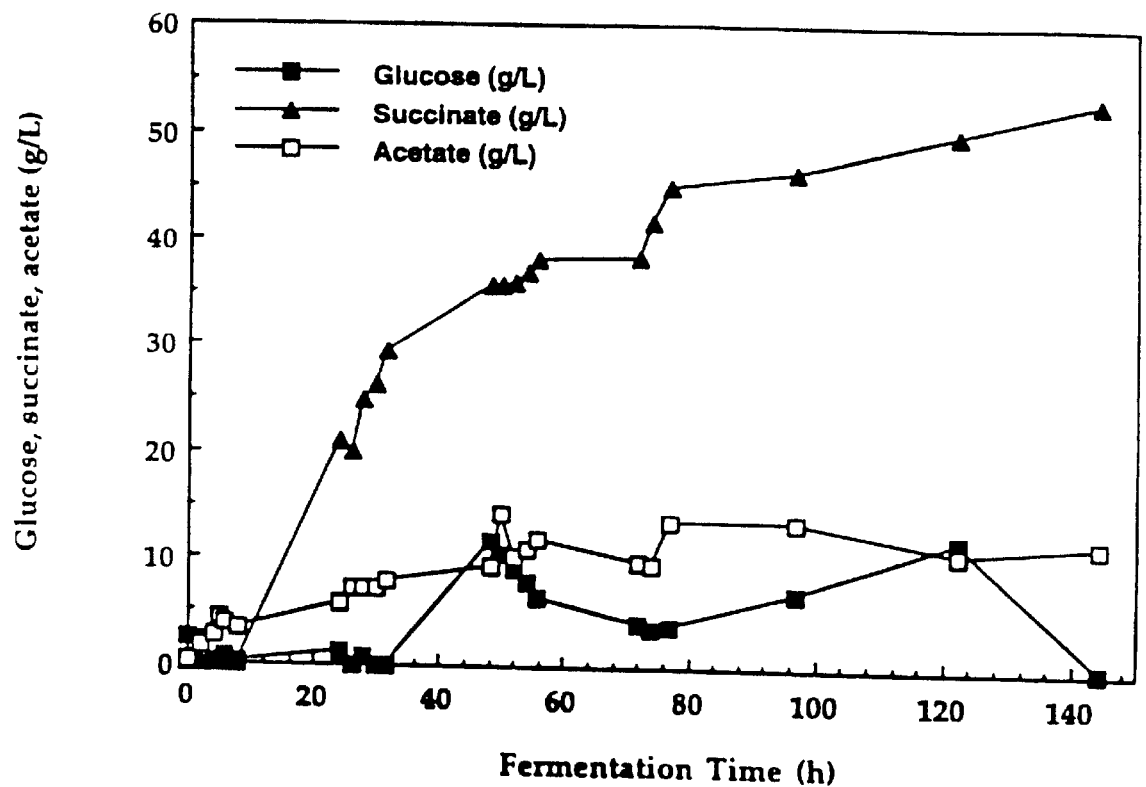
FIG. 5 shows the results of the experiment described in EXAMPLE 5.

The results are plotted in FIG. 5 and summarized in TABLE 8. TABLE 8 shows the accumulation of succinic acid in 25% light steep water fermentation medium.

TABLE 8

| Fermentation time (h) | 24 | 48 | 97 |
|---|---|---|---|
| Succinic acid concentration (g/L) | 20.9 | 35.7 | 46.3 |
| Productivity (g/L-h) | 0.87 | 0.74 | 0.48 |

The results indicated that succinic acid could be produced in an even more economical medium in which the light steep water was reduced to 25%.

EXAMPLE 6

In this example, the light steep water concentration in both the shakeflask and fermentation media was 25% and the base was 1.5M ammonium carbonate. Other conditions were the same as described in EXAMPLE 4.

Figure 6:
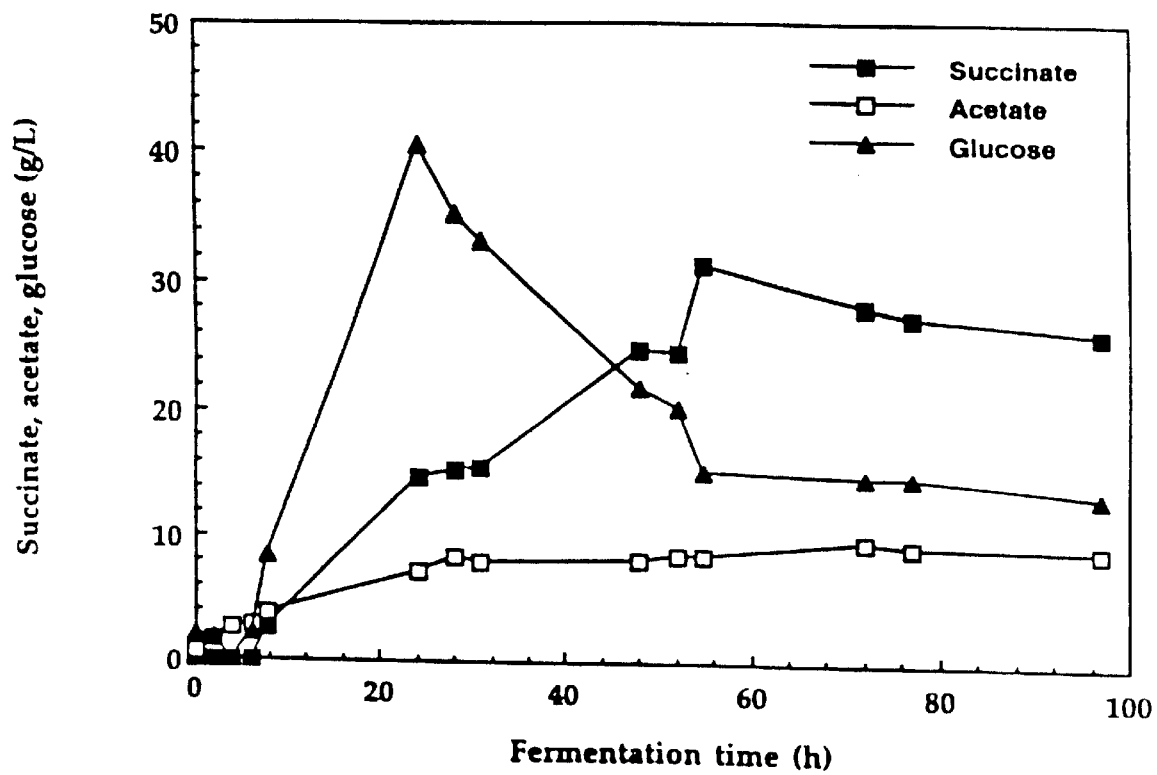
FIG. 6 shows the results of the experiments described in EXAMPLE 6.

The results are plotted in FIG. 6 and summarized in TABLE 9 which shows the accumulation of succinic acid in 25% light steep water fermentation medium with ammonium carbonate for pH control.

TABLE 9

| Fermentation time (h) | 24 | 48 |
|---|---|---|
| Succinic acid concentration (g/L) | 14.8 | 24.9 |
| Productivity (g/L-h) | 0.62 | 0.52 |

The results indicated that carbonate salts other than sodium carbonate, such as ammonium carbonate, magnesium carbonate, etc. could be used for pH control in a succinic acid fermentation process.

EXAMPLE 7

Four experiments are described in this example. In two experiments, the light steep water concentration in both the shakeflask and fermentation media was 25% and the base was 2M NaOH. In the other two experiments, the light steep water concentration was 50% and the base was 15% $NH_4OH$. Within each set of two experiments which used the same base for pH control, pure carbon dioxide was sparged into the fermenter at about 100 mL per minute in one experiment during the anaerobic phase for the production of succinic acid by anaerobic metabolism.

Figure 7:
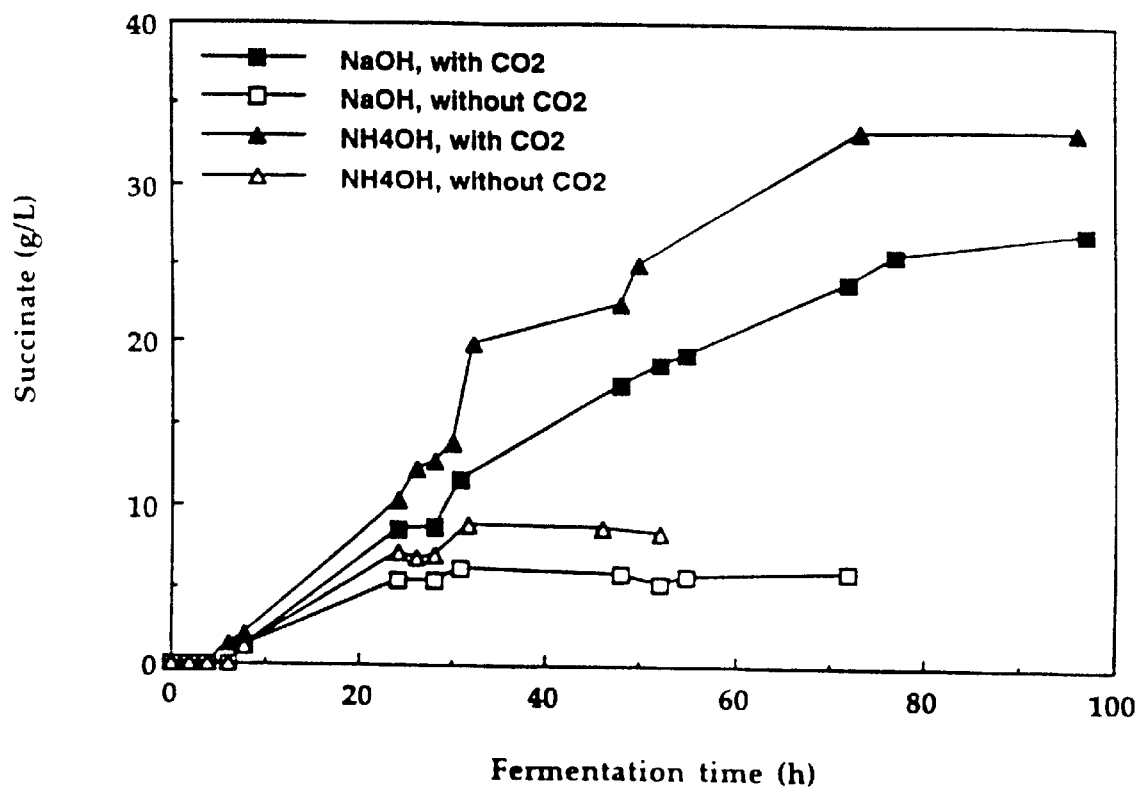
FIG. 7 shows the results of the experiments described in EXAMPLE 7.

The results are plotted in FIG. 7 and summarized in TABLE 10. TABLE 10 shows the accumulation of succinic acid in light steep water fermentation medium with ammonium hydroxide and sodium hydroxide for pH control.

TABLE 10

| | With $CO_2$ | | Without $CO_2$ | |
|---|---|---|---|---|
| Base = NaOH | | | | |
| Fermentation time (h) | 48 | 72 | 48 | 72 |
| Succinic acid concentration (g/L) | 17.5 | 23.9 | 6.0 | 6.0 |
| Productivity (g/L-h) | 0.36 | 0.33 | 0.13 | 0.08 |

TABLE 10-continued

| | With CO$_2$ | | Without CO$_2$ | |
|---|---|---|---|---|
| Base = NH$_4$OH | | | | |
| Fermentation time (h) | 48 | 72 | 46 | 52 |
| Succinic acid concentration (g/L) | 22.5 | 33.4 | 8.7 | 8.4 |
| Productivity (g/L-h) | 0.47 | 0.46 | 0.19 | 0.16 |

The results indicated that if a base other than a carbonate salt was used for pH control, sparging of carbon dioxide gas into the fermenter during the anaerobic phase would be needed for significant succinic acid production.

The present invention also provides for a method for producing malic acid via fermentation. Malic acid, a precursor of succinic acid is in principle a better end product than succinic acid, in as much as its production requires one less reductive step. The theoretical stoichiometry for malic acid production is one mole of glucose and two moles of carbon dioxide converted to two moles of malic acid. As such, the production of malic acid can occur without waste of glucose. Fumaric acid, which is the dehydration product of malic acid and the precursor of succinate in the reduction pathway, can also be formed. Both malic acid and fumaric acid also can be formed without the production of co-product, but the higher solubility of malic acid makes it preferable for large scale production processes.

The present invention can also be a continuous fermentation process which consists of a fermenter and a settling tank. The cells which settle at the bottom of the settling tank are returned to the fermenter to increase cell concentration which in turn increases productivity. It has been observed that the cells flocculated and settled extremely well when mixing was stopped.

Succinic acid is also produced through a continuous fermentation process which consists of a fermenter and an ultra-filtration unit. The cells collected in this unit are returned to the fermenter to increase cell concentration which in turn increases productivity. The removal of fermentation product(s) from the broth by the ultra-filtration unit relieves product inhibition and increases yield.

Succinic acid is also produced through a continuous fermentation process in which an adsorbent is added to and removed from the fermenter continuously. The removal of fermentation product(s) from the broth relieves product inhibition and increases yield.

Succinic acid is also produced through a batch process consisting of two fermenters in series. The organism is grown under aerobic conditions in the first fermenter (growth fermenter) to high cell density. The biomass is then transferred to the second fermenter (production fermenter) where anaerobic conditions are applied to promote the production of succinic acid. The growth fermenter then can be cleaned and used to grow more biomass for transfer to another production fermenter. Since the production time is much longer than the growth time, one growth fermenter can be used to provide biomass for a number of production fermenters.

DEPOSIT OF MICROORGANISMS

The applicants, in accordance with the provisions of the Budapest treaty on the international recognition of the deposit of microorganisms for the purposes of patent procedure under the Budapest Treaty, did deposit samples of AFP111 with the American Type Culture Collection (ATCC), 12301 Parklawn Drive, Rockville, Md. 20852, U.S.A. on Aug. 20, 1997 and assigned ATCC deposit reference Number 202021. The culture is hereby irrevocably and without restriction or condition released to the public upon the issuance of letters patent herefor.

While there has been shown and described what are at present considered the preferred embodiments of the invention, it will be obvious to those skilled in the art that various changes and modifications can be made therein, without departing from the scope of the invention defined by the appended claims.

What is claimed is:

1. A method for producing carboxylic acids comprising the steps of:
    a) inoculating a medium having a carbon source with a carboxylic acid-producing organism having a biomass;
    b) incubating said organism in an aerobic atmosphere to promote rapid growth of said organism thereby increasing said biomass of said organism;
    c) controllably releasing oxygen to maintain said aerobic atmosphere;
    d) controllably feeding said organism a solution containing said carbon source to maintain a concentration of said carbon source within said medium of about 0.5 g/L up to about 1 g/L;
    e) depriving said aerobic atmosphere of said oxygen to produce an anaerobic atmosphere to cause said organism to undergo anaerobic metabolism;
    f) controllably feeding said organism said solution containing said carbon source to maintain a concentration of said carbon source within said medium of $\geq 1$ g/L; and
    g) converting said carbon source to carboxylic acids using said anaerobic metabolism of said organism.

2. The method of claim 1 wherein said organism is selected from the group consisting of *Escherichia coli* and Lactobacillus bacteria.

3. The method of claim 1 wherein said organism is osmotolerant whereby said organism is capable of producing organic acids without any inhibition of the metabolism of said organism.

4. The method of claim 2 wherein said *Escherichia coli* is AFP-111.

5. The method of claim 2 wherein said organism is an *Escherichia coli* bacteria derived from a parent organism lacking the genes for pyruvate formate lyase and lactate dehydrogenase.

6. The method of claim 1 wherein said organism is genetically manipulated to express an enzyme which enables said organism to convert pyruvate to dicarboxylic acid.

7. The method of claim 6 wherein said enzyme is malic enzyme.

8. The method of claim 7 wherein said organism using said anaerobic metabolism produces succinic acid, acetic acid and ethanol, wherein said succinic acid being the main product.

9. The method of claim 7 wherein said organism using said anaerobic metabolism produces malic acid, acetic acid and ethanol, wherein said malic acid being the main product.

10. The method of claim 7 wherein said organism using said anaerobic metabolism produces fumaric acid, acetic acid and ethanol, wherein said fumaric acid being the main product.

11. A method for producing carboxylic acids comprising:
    a) inoculating a medium having a carbon source with a carboxylic acid-producing organism having a biomass;

b) incubating said organism in an environment having a maintained pH value and having an aerobic atmosphere to promote rapid growth of said organism thereby increasing said biomass of said organism;

c) controllably releasing oxygen to maintain said aerobic atmosphere;

d) controllably feeding said organism a solution containing said carbon source to maintain a concentration of said carbon source within said medium of about 0.5 g/L up to about 1 g/L;

e) transferring said organism having increased biomass to a production fermenter having an anaerobic atmosphere to cause said organism to undergo anaerobic metabolism;

f) controllably feeding said organism a solution containing said carbon source to maintain a concentration of said carbon source within said production fermenter of $\geq 1$ g/L; and g) converting said carbon source to carboxylic acids using said anaerobic metabolism of said organism.

12. The method of claim 11 wherein said organism is selected from the group consisting of *Escherichia coli* and Lactobacillus bacteria.

13. The method of claim 11 wherein said organism is osmotolerant whereby said organism is capable of producing organic acids without any inhibition of the metabolism of said organism.

14. The method of claim 12 wherein said *Escherichia coli* is AFP-111.

15. The method of claim 12 wherein said organism is an *Escherichia coli* strain derived from a parent organism lacking the genes for pyruvate formate lyase and lactate dehydrogenase.

16. The method of claim 11 wherein said organism is genetically manipulated to express an enzyme which enables said organism to convert pyruvate to dicarboxylic acid.

17. The method of claim 16 wherein said enzyme is malic enzyme.

18. The method of claim 17 wherein said organism using said anaerobic metabolism produces succinic acid, acetic acid and ethanol, wherein said succinic acid being the main product.

19. The method of claim 17 wherein said organism using said anaerobic metabolism produces malic acid, acetic acid and ethanol, wherein said malic acid being the main product.

20. The method of claim 17 wherein said organism using said anaerobic atmosphere produces fumaric acid, acetic acid and ethanol, wherein said fumaric acid being the main product.

* * * * *